United States Patent [19]

McKibbin

[11] Patent Number: 5,190,881
[45] Date of Patent: Mar. 2, 1993

US005190881A

[54] DETERMINATION OF ACTINIDES IN URINE AND FECAL SAMPLES

[75] Inventor: Terry T. McKibbin, Larimer County, Colo.

[73] Assignee: The United States of America as represented by the United States Department of Energy, Washington, D.C.

[21] Appl. No.: 831,017

[22] Filed: Feb. 4, 1992

[51] Int. Cl.$^5$ ............................................. G01N 33/20
[52] U.S. Cl. ....................... 436/82; 436/57; 436/74; 436/81; 436/175; 436/177; 422/68.1
[58] Field of Search ............. 436/82, 57, 74, 81, 436/175, 177; 422/68.1

[56] References Cited

U.S. PATENT DOCUMENTS 4,835,107  5/1989  Horowitz et al. ................. 436/82

OTHER PUBLICATIONS

Holm et al. *Talanta*, vol. 23, pp. 853-855, 1976. "Determination of Americum and Curium by Using ion-exchange in Nitric acid-methanol medium for environmental analysis".

Kressin, *Analytical Chemistry*, vol. 53, 1981, pp. 1270-1274. "Separation of Plutonium in Urine without Sample Ashing for Determination by $\alpha$-Spectrometry".

Hindman *Analytical Chemistry*, vol. 55, 1983, pp. 2460-2461. "Neodymium Fluoride Mounting for $\alpha$ Spectrometric Determination of Uranium, Plutonium, and Americium".

Hindman, *Analytical Chemistry*, vol. 58, 1986, pp. 1238-1241. "Actinide Separations for $\alpha$-Spectrometry Using Neodymium Fluoride Coprecipitation".

*Primary Examiner*—James C. Housel
*Assistant Examiner*—Maureen M. Wallenhorst
*Attorney, Agent, or Firm*—James W. Weinberger; Thomas G. Anderson; William R. Moser

[57] ABSTRACT

A method of determining the radioactivity of specific actinides that are carried in urine or fecal sample material is disclosed. The samples are ashed in a muffle furnace, dissolved in an acid, and then treated in a series of steps of reduction, oxidation, dissolution, and precipitation, including a unique step of passing a solution through a chloride form anion exchange resin for separation of uranium and plutonium from americium.

10 Claims, No Drawings

DETERMINATION OF ACTINIDES IN URINE AND FECAL SAMPLES

CONTRACTUAL ORIGIN OF THE INVENTION

The United States Government has rights in this invention pursuant to Contract No. DE-AC07-84ID12435 between the United States Department of Energy and Westinghouse Idaho Nuclear Company, Inc.

FIELD OF THE INVENTION

This invention relates to a method of separating and then analyzing urine and fecal samples for trace amounts of uranium (U), plutonium (Pu), and americium (Am) within the same sample.

BACKGROUND OF THE INVENTION

In the event of ingestion of certain radioactive actinides, it is desirable to monitor the discharge or release of these actinides by counting on an alpha spectrometer the body discharges within both urine and fecal matter.

In the case of urine, the sample is boiled to dryness in an acid. The dried urine sample is then ashed in a muffle furnace and then dissolved in another acid. The actinides are then gathered on a ferric oxide precipitate.

In the case of a fecal sample, there is a similar sample preparation process consisting of drying, ashing in the muffle oven, treating the ash with a mixture of acids and then precipitating with a ferrous phosphate.

In a prior art, fecal sample procedure developed for the Department of Energy, identified as USDOE, RESL/ID, A-16, 1981, the precipitate carrying the actinides is reprecipitated on calcium fluoride thereby further separating the actinides from aluminum, iron, titanium, and protactinium. The calcium fluoride is dissolved in acidic aluminum nitrate, and the actinide series elements thorium through plutonium are extracted into a quaternary amine. Selective back extractions further separate the actinides from each other. The uranium accompanies the plutonium through the extraction but is separated from the plutonium in the cerium fluoride precipitation step; the uranium staying in the filtrate. The uranium can be recovered by the addition of titanous chloride and more cerium carrier to the fluoride filtrate. All fractions are electrodeposited, or carried on cerium fluoride, on filter paper, and analyzed by alpha spectrometry for isotopic identification and quantification.

The DOE process creates some hazardous wastes, including perchlorated organic liquid, i.e., aliphatic quaternary amine.

It is, therefore, a purpose of this invention to provide a simpler, cost effective procedure that generates less hazardous wastes that can be easily disposed.

SUMMARY OF THE INVENTION

The invention generally stated is a process for analyzing urine and feces for trace amounts of actinides, i.e. uranium (U), plutonium (Pu), and americium (Am) by use of a chloride form anion exchange resin consisting of:

dissolving a precipitate containing the actinides in a solution of hydrochloric acid (HCl) and hydrofluoric acid (HF);

reducing the dissolved precipitate;

adding a neodymium (Nd) carrier, thereby forming a neodymium fluoride (NdF) precipitate;

dissolving the NdF precipitate, adding ammonium hydroxide and reprecipitating as neodymium hydroxide $(Nd(OH)_3)$;

dissolving the $Nd(OH)_3$ precipitate in a dilute nitric acid $(HNO_3)$;

treating the dissolved $Nd(OH)_3$ with sodium nitrite, thereby adjusting the oxidation state of the plutonium (Pu) to a valence of four (IV);

reprecipitating the dissolved $Nd(OH)_3$ by the addition of ammonium hydroxide $(NH_4OH)$;

dissolving the reprecipitated $Nd(OH)_3$ by the addition of hydrochloric acid;

passing the dissolved $Nd(OH)_3$ through a chloride form anion exchange resin;

washing the resin in hydrochloric acid, thereby removing americium (Am) and salts from the resin;

eluting the uranium (U) and plutonium (Pu) with a 1 M hydrochloric acid and adding an Nd carrier;

adding hydrofluoric acid (HF) to the eluant, thereby forming a neodymium fluoride (NdF) precipitate carrying tetravalent plutonium (Pu);

filtering the NdF precipitate, thereby forming a filtered precipitate and a filtrate;

counting a plutonium activity of the filtered precipitate on an alpha spectrometer;

treating the filtrate with titanium trichloride $(TiCl_3)$ thereby reducing the uranium;

adding a neodymium carrier to the filtrate thereby forming a NdF precipitate carrying uranium;

filtering the NdF precipitate;

counting a uranium activity of the filtered precipitate on the alpha spectrometer;

adding ammonium hydroxide to a remaining eluant portion, thereby forming a precipitate carrying americium;

dissolving the precipitate;

complexing the americium with EDTA forming a solution;

neutralizing the solution with ammonium hydroxide and discarding the precipitate;

coprecipitating the americium on a neodymium hydroxide precipitate using potassium hydroxide;

oxidizing the americium to a valence of six (VI);

selectively reducing any cerium present;

precipitating the neodymium fluoride (NdF);

centrifuging and discarding the NdF precipitate;

reducing the Am (VI) to Am (III);

adding an Nd carrier;

letting the solution stand for 15 minutes;

filtering on a 0.1 $\mu$m filter; and then counting an americium activity of the filtered precipitate on the alpha spectrometer.

Other objects, advantages, and capabilities of the present invention will become more apparent as the description proceeds.

DETAILED DESCRIPTION OF THE INVENTION

Urine is initially treated by boiling to dryness with nitric acid. The dry organic material is destroyed in a muffle furnace, and the resulting residue is dissolved in dilute hydrochloric acid. The actinides are then gathered on a ferric hydroxide precipitate.

The initial treatment of the fecal sample is generally described as follows. The fecal sample is dried on a hot plate, ignited, and muffled in a furnace at 550° C. for sixteen hours. Up to five grams of ash is treated with hydrochloric, nitric, perchloric, and hydrofluoric acids to remove organic and siliceous material. The slurry of salts remaining are taken through a pyrophosphate fusion on a hot plate to facilitate the complete dissolution in 2 Molar (M) HCl. Iron(III) is added to act as a carrier. A reduction is performed using ascorbic acid and titanium trichloride. The sample pH is carefully adjusted to 3.0-3.5 with ammonium hydroxide which precipitates iron(II) phosphate. The americium, reduced uranium, and plutonium are carried on the iron phosphate precipitate.

The precipitate containing the actinides from either of the above initial treatments is dissolved in a 2M HCl and HF solution. A reduction is performed using $TiCL_3$, a neodymium carrier is added, and the actinides are gathered on the precipitated neodymium fluoride. The fluoride precipitate is dissolved in a nitric/boric acid mixture and reprecipitated as $Nd(OH)_3$. The hydroxide precipitate is dissolved in dilute nitric acid, and the solution is treated with sodium nitrite to adjust the oxidation state of the plutonium to a valence of four, IV.

Neodymium hydroxide is reprecipitated using ammonium hydroxide and then dissolved with HCl to obtain an 8-10M HCl solution. The solution is passed through a 100-200 mesh 1-X8 chloride form anion exchange resin manufactured by Bio-Rad Co. using a 4 cm × 1 cm diameter column. The 1-X8 resin refers to a cross-linking within the resin structure. The resin is washed with up to 25 mL of 10M HCl to remove americium and salts from the resin. The uranium and plutonium are elutriated together with 10-12 mL of 1M HCl.

The plutonium and uranium are separated using sequential neodymium fluoride precipitations. Fifty micrograms of neodymium and 1-2 mL of hydrofluoric acid is added to the eluant. Neodymium fluoride precipitates carrying the tetravalent plutonium. The precipitate is filtered onto a 0.1 micron membrane filter and subsequently counted on an alpha spectrometer. The filtrate containing the uranium is treated with $TiCl_3$ to reduce the uranium, and another 50 micrograms of neodymium carrier is added. The neodymium fluoride containing the uranium is collected on a 0.1 micron membrane filter and counted as above.

The americium is coprecipitated on a neodymium hydroxide precipitate. The precipitate is dissolved, the americium complexed with EDTA, and the solution is barely neutralized to precipitate interfering cations. The americium is then gathered on a neodymium hydroxide precipitate using strong base, such as potassium hydroxide. The final clean-up from the rare earths and thorium employs an oxidation of the americium to the VI valence and precipitation of the thorium and rare earths as fluorides. A selective reduction and a neodymium fluoride precipitation are used to gather the americium for counting using alpha spectrometry.

The process above creates wastes as follows: aqueous acids and bases and solid anion exchange resin, which are more easily disposed of.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

What is claimed is:

1. A method for analyzing human urine or feces for trace amounts of actinides, consisting of uranium (U), plutonium (Pu), and americium (Am) in a single sample of urine or feces, said sample having been dried, reduced, and carried on a first precipitate, comprising the steps of:

(a.) dissolving the first precipitate in a solution of hydrochloric acid (HCl) and hydrofluoric acid (HF);

(b.) reducing the dissolved precipitate of step (a.) by the addition of titanium trichloride ($TiCl_3$);

(c.) adding a neodymium (Nd) carrier, thereby forming a neodymium fluoride (NdF) precipitate;

(d.) dissolving the NdF precipitate in a mixture of nitric acid ($HNO_3$) and boric acid ($H_3BO_3$), adding ammonium hydroxide and reprecipitating as neodymium hydroxide ($Nd(OH)_3$);

(e.) dissolving the $Nd(OH)_3$ precipitate in a dilute nitric acid ($HNO_3$);

(f.) treating the dissolved $Nd(OH)_3$ with sodium nitrite ($NaNO_2$), thereby adjusting the oxidation state of the plutonium (Pu) to a valence of four (IV);

(g.) reprecipitating the dissolved $Nd(OH)_3$ of step (f.) by the addition of ammonium hydroxide ($NH_4OH$);

(h.) dissolving the reprecipitated $Nd(OH)_3$ of step (g.) by the addition of hydrochloric acid (HCl);

(i.) passing the dissolved $Nd(OH)_3$ of step (h.) through an anion exchange resin;

(j.) washing the resin of step (i.) in hydrochloric acid, thereby removing americium (Am) and salts from the resin;

(k.) eluting the uranium (U) and plutonium (Pu) with a 1M hydrochloric acid;

(l.) adding hydrofluoric acid (HF) to the eluant of step (k.), thereby forming a neodymium fluoride (NdF) precipitate carrying tetravalent plutonium (Pu);

(m.) filtering the NdF precipitate of step (l.) thereby forming a filtered precipitate and a filtrate;

(n.) counting a plutonium activity of the filtered precipitate of step (m.) on an alpha spectrometer;

(o.) treating the filtrate of step (m.) with titanium trichloride ($TiCl_3$), thereby reducing the uranium;

(p.) adding a neodymium carrier to the filtrate of step (o.), thereby forming a NdF precipitate carrying uranium;

(q.) filtering the NdF precipitate of step (p.);

(r.) counting a uranium activity of the filtered precipitate of step (q.) on the alpha spectrometer;

(s.) adding ammonium hydroxide to the eluant portion from step (j.), thereby forming a precipitate carrying americium;

(t.) dissolving the precipitate of step (s.);

(u.) complexing the dissolved precipitate of step (t.) with ethylene diamine-tetraacetic acid (EDTA) thereby forming a solution;

(v.) neutralizing the solution of step (u.) with ammonium hydroxide and discarding the precipitate formed;

(w.) coprecipitating the americium on a neodymium hydroxide precipitate by the addition of potassium hydroxide;

(x.) oxidizing the americium to a valence of six (VI) thereby redissolving the precipitates of step (w.)

(y.) selectively reducing any cerium (Ce) present;

(z.) precipitating the neodymium as neodymium fluoride (NdF);

(aa.) centrifuging the NdF precipitate of step (z.) and discarding the NdF precipitate;

(bb.) reducing the Am (VI) to Am (III);
(cc.) adding an Nd carrier;
(dd.) letting a solution of step (cc.) stand for 15 minutes;
(ee.) filtering a precipitate on a 0.1 μm filter; and then
(ff.) counting an americium activity of the filtered precipitate of step (ee.) on the alpha spectrometer.

2. The method as recited in claim 1 wherein:
the first precipitate is an iron phosphate and the sample is human feces.

3. The method as recited in claim 1 wherein:
the solution of step (a.) of HCl and HF has a molarity of 2M.

4. The method as recited in claim 1 wherein:
the reprecipitated $Nd(OH)_3$ of step (h.) has a molarity (M) of about 8–10M.

5. The method as recited in claim 1 wherein:
the dissolved $Nd(OH)_3$ of step (i.) is passed through a resin column having a mesh size of between 100 and 200.

6. The method as recited in claim 1 wherein:
the molarity of the HCl used to wash the resin of step (j.) is 10M.

7. The method as recited in claim 1 wherein:
the resin of step (i.) is a chloride form anion exchange resin.

8. The method as recited in claim 1 wherein:
the first precipitate is a ferric hydroxide and the sample is urine.

9. A method for analyzing human urine for trace amounts of actinides, consisting of uranium (U), plutonium (Pu), and americium (Am) in a single sample of human urine, said sample having been dried, reduced, and carried on a ferric hydroxide precipitate, comprising the steps of:

(a.) dissolving the ferric hydroxide precipitate in a solution of hydrochloric acid (HCl) and hydrofluoric acid (HF);
(b.) reducing the dissolved precipitate of step (a.) by the addition of titanium trichloride ($TiCl_3$);
(c.) adding a neodymium (Nd) carrier, thereby forming a neodymium fluoride (NdF) precipitate;
(d.) dissolving the NdF precipitate in a mixture of nitric acid ($HNO_3$) and boric acid ($H_3BO_3$), adding ammonium hydroxide and reprecipitating as neodymium hydroxide ($Nd(OH)_3$);
(e.) dissolving the $Nd(OH)_3$ precipitate in a dilute nitric acid ($HNO_3$);
(f.) treating the dissolved $Nd(OH)_3$ with sodium nitrite ($NaNO_2$), thereby adjusting the oxidation state of the plutonium (Pu) to a valence of four (IV);
(g.) reprecipitating the dissolved $Nd(OH)_3$ of step (f.) by the addition of ammonium hydroxide ($NH_4OH$);
(h.) dissolving the reprecipitated $Nd(OH)_3$ of step (g.) by the addition of hydrochloric acid (HCl);
(i.) passing the dissolved $Nd(OH)_3$ of step (h.) through an anion exchange resin;
(j.) washing the resin of step (i.) in hydrochloric acid, thereby removing americium (Am) and salts from the resin;
(k.) eluting the uranium (U) and plutonium (Pu) with a 1M hydrochloric acid;
(l.) adding hydrofluoric acid (HF) to the eluant of step (k.), thereby forming a neodymium fluoride (NdF) precipitate carrying tetravalent plutonium (Pu);
(m.) filtering the NdF precipitate of step (l.) thereby forming a filtered precipitate and a filtrate;
(n.) counting a plutonium activity of the filtered precipitate of step (m.) on an alpha spectrometer;
(o.) treating the filtrate of step (m.) with titanium trichloride ($TiCl_3$), thereby reducing the uranium;
(p.) adding a neodymium carrier to the filtrate of step (o.), thereby forming a NdF precipitate carrying uranium;
(q.) filtering the NdF precipitate of step (p.);
(r.) counting a uranium activity of the filtered precipitate of step (q.) on the alpha spectrometer;
(s.) adding ammonium hydroxide to the eluant portion from step (j.), thereby forming a precipitate carrying americium;
(t.) dissolving the precipitate of step (s.);
(u.) complexing the dissolved precipitate of step (t.) with ethylene diamine-tetraacetonitrite acid (EDTA) thereby forming a solution;
(v.) neutralizing the solution of step (u.) with ammonium hydroxide and discarding the precipitate formed;
(w.) coprecipitating the americium on a neodymium hydroxide precipitate by the addition of potassium hydroxide;
(x.) oxidizing the americium to a valence of six (VI) thereby redissolving the precipitates of step (w.).
(y.) selectively reducing any cerium (Ce) present;
(z.) precipitating the neodymium as neodymium fluoride (NdF);
(aa.) centrifuging the NdF precipitate of step (z.) and discarding the precipitate;
(bb.) reducing the Am (VI) to Am (III);
(cc.) adding an Nd carrier;
(dd.) letting a solution of step (cc.) stand for 15 minutes;
(ee.) filtering a precipitate on a 0.1 μm filter; and then
(ff.) counting an americium activity of the filtered precipitate of step (ee.) on the alpha spectrometer.

10. A method for analyzing human feces for trace amounts of actinides, consisting of uranium (U), plutonium (Pu), and americium (Am) in a single sample of human feces, said sample having been dried, reduced, and carried on an iron phosphate precipitate, comprising the steps of:

(a.) dissolving the iron phosphate precipitate in a solution of hydrochloric acid (HCl) and hydrofluoric acid (HF);
(b.) reducing the dissolved precipitate of step (a.) by the addition of titanium trichloride ($TiCl_3$);
(c.) adding a neodymium (Nd) carrier, thereby forming a neodymium fluoride (NdF) precipitate;
(d.) dissolving the NdF precipitate in a mixture of nitric acid ($HNO_3$) and boric acid ($H_3BO_3$), adding ammonium hydroxide and reprecipitating as neodymium hydroxide ($Nd(OH)_3$);
(e.) dissolving the $Nd(OH)_3$ precipitate in a dilute nitric acid ($HNO_3$);
(f.) treating the dissolved $Nd(OH)_3$ with sodium nitrite ($NaNO_2$), thereby adjusting the oxidation state of the plutonium (Pu) to a valence of four (IV);
(g.) reprecipitating the dissolved $Nd(OH)_3$ of step (f.) by the addition of ammonium hydroxide ($NH_4OH$);
(h.) dissolving the reprecipitated $Nd(OH)_3$ of step (g.) by the addition of hydrochloric acid (HCl);
(i.) passing the dissolved $Nd(OH)_3$ of step (h.) through an anion exchange resin;

(j.) washing the resin of step (i.) in hydrochloric acid, thereby removing americium (Am) and salts from the resin;
(k.) eluting the uranium (U) and plutonium (Pu) with 1M hydrochloric acid;
(l.) adding hydrofluoric acid (HF) to the eluant of step (k.), thereby forming a neodymium fluoride (NdF) precipitate carrying tetravalent plutonium (Pu);
(m.) filtering the NdF precipitate of step (l.), thereby forming a filtered precipitate and a filtrate;
(n.) counting a plutonium activity of the filtered precipitate of step (m.) on an alpha spectrometer;
(o.) treating the filtrate of step (m.) with titanium trichloride (TiCl$_3$), thereby reducing the uranium;
(p.) adding a neodymium carrier to the filtrate of step (o.), thereby forming a NdF precipitate carrying uranium;
(q.) filtering the NdF precipitate of step (p.);
(r.) counting a uranium activity of the filtered precipitate of step (q.) on the alpha spectrometer;
(s.) adding ammonium hydroxide to the eluant portion from step (j.) thereby forming a precipitate carrying americium;
(t.) dissolving the precipitate of step (s.);
(u.) complexing the dissolved precipitate of step (t.) with ethylene diamine-tetraacetic acid (EDTA) thereby forming a solution;
(v.) neutralizing the solution of step (u.) with ammonium hydroxide and discarding the precipitate formed;
(w.) coprecipitating the americium on a neodymium hydroxide precipitate by the addition of potassium hydroxide;
(x.) oxidizing the americium to a valence of six (VI) thereby redissolving the precipitates of step (w.);
(y.) selectively reducing any cerium (Ce) present;
(z.) precipitating the neodymium as neodymium fluoride (NdF);
(aa.) centrifuging and discarding the NdF precipitate of step (z.);
(bb.) reducing the Am (VI) to Am (III);
(cc.) adding an Nd carrier;
(dd.) letting a solution of step (cc.) stand for 15 minutes;
(ee.) filtering a precipitate on a 0.1 μm filter; and then
(ff.) counting an americium activity of the filtered precipitate of step (ee.) on the alpha spectrometer.

* * * * *